United States Patent [19]
Hamied et al.

[11] Patent Number: 5,929,030
[45] Date of Patent: Jul. 27, 1999

[54] PHARMACEUTICAL COMPOSITIONS

[75] Inventors: Y. K. Hamied; Geena Malhotra; V. G. Nayak, all of Mumbai, India

[73] Assignee: Byron Fine Chemicals Inc., Long Island City, N.Y.

[21] Appl. No.: 08/697,204

[22] Filed: Aug. 21, 1996

[30] Foreign Application Priority Data

Aug. 30, 1995 [EP] European Pat. Off. .............. 95306022

[51] Int. Cl.$^6$ .................................................. A61K 37/00
[52] U.S. Cl. ...................................................... 514/9
[58] Field of Search ................................................... 514/9

[56] References Cited

FOREIGN PATENT DOCUMENTS

| 0327280 | 8/1989 | European Pat. Off. . |
|---|---|---|
| 0429248 | 5/1991 | European Pat. Off. . |
| 0521799 | 1/1993 | European Pat. Off. . |
| 0589843 | 3/1994 | European Pat. Off. . |
| 0651995 | 5/1995 | European Pat. Off. . |
| 2636534 | 3/1990 | France . |
| 3235706 | 1/1984 | Germany . |
| 93/18752 | 9/1993 | WIPO . |

OTHER PUBLICATIONS

Chemical Abstracts 123:179540. Friedman et al. 1992.

*Primary Examiner*—Zohreh Fay
*Attorney, Agent, or Firm*—Dilworth & Barrese

[57] ABSTRACT

Water-insoluble pharmaceutically active substances such as cyclosporin are formulated for administration in the form of an oil-in-water microemulsion, wherein the active substance is fully dissolved in the dispersed oil particles. The oil is $C_8$ to $C_{20}$ fatty acid vegetable oil glycerides, and lecithin and another surfactant are included to form and stabilize the microemulsion in which the hydrophilic phase comprises propylene glycol. A preconcentrate comprising the above components but free from any hydrophilic phase can be utilized to make up the compositions, which are most suitably soft gelatine capsules or oral administration fluids. The glycerides are preferably from castor oil, coconut oil or peanut oil.

28 Claims, No Drawings

PHARMACEUTICAL COMPOSITIONS

BACKGROUND OF THE INVENTION

This invention relates to pharmaceutical compositions for the administration of water-insoluble pharmaceutically active substances.

There are a number of pharmaceutically active substances which are water-insoluble and which, as a result, present a number of problems for their safe administration and bioavailability. Among such substances are the cyclosporins, and water-insoluble peptides, antimicrobials and antineoplastics, for example. There have been many proposals of pharmaceutical formulations for the administration of the cyclosporins, some of which are described in the following patent specifications: WO92/09299, GB-A-2015339, GB-A-2270842, WO94/08610, WO92/18105, GB-A-2228198, U.S. Pat. No. 4,388,307, GB-A-2222770, EP-A-0539319 and EP-A-0589843.

In general, because the cyclosporins are hydrophobic, pharmaceutical compositions containing them usually comprise lipophilic materials such as oils. GB-A-2228198 describes, for example, pharmaceutical compositions containing cyclosporin in a carrier medium of a fatty acid triglyceride, a glycerol fatty acid partial ester or propyleneglycol or sorbitol complete or partial ester, and a surface active agent having an HLB of at least 10. These oil-based compositions are not intended to be emulsified in water but are used as such, and are preferably free of ethanol.

Other cyclosporin compositions are known which contain not only hydrophobic oils but also hydrophilic materials such as propylene glycol and ethanol in which cyclosporins are soluble. There compositions are in the form of emulsions. Emulsions have certain advantages over oil-based single phase compositions, and EP-A-0589843 describes some cyclosporin emulsion compositions containing, as the carrier medium, a hydrophilic organic solvent, a mixed mono-, di- and tri-glyceride or a transesterified and polyethoxylated vegetable oil, a polyoxyethylene sorbitan-fatty acid ester surfactant, and an aqueous phase. The carrier medium with the cyclosporin but without the aqueous phase is described as an emulsion preconcentrate.

In recent times, microemulsions have been developed for cyclosporin administration and these have provided provided further advantages over the prior known (coarse) emulsions, especially for oral administration formulations. It is also known to provide so-called "micro-emulsion preconcentrates". For example, GB-A-2222770 describes a pharmaceutical microemulsion preconcentrate composition comprising cyclosporin, a hydrophilic phase, a lipophilic phase and a surfactant. This preconcentrate is converted to a microemulsion by adding water or another suitable aqueous medium.

These and other microemulsions for cyclosporin are all made by dissolving the cyclosporin in a hydrophilic phase e.g. propylene glycol, and then mixing the solution with the oil and eventually with an aqueous phase. We have found that there can be a tendency with these microemulsions for solid microfine cyclosporin to be formed during their use, e.g. after administration. This is basically undesirable, and we have now found that microemulsions can be made in which this tendency is very much reduced or totally absent.

SUMMARY OF THE INVENTION

In particular, we have found that if the water-insoluble active substance is first dissolved directly in the lipophilic phase, rather than in a hydrophilic phase, and then the oil-in-water microemulsion produced therefrom, the substance remains in solution in the lipophilic (oil) phase. This phase is distributed throughout the aqueous phase of the microemulsions as very tiny particles, and it appears that in this way the substance can be taken up very easily and efficiently by the body. In addition, there is no precipitation of the substance out of the oil solution.

In one aspect the present invention provides a pharmaceutical composition in the form of a stable oil-in-water microemulsion, which composition comprises a) a water-insoluble pharmaceutically active material;

b) $C_8$ to $C_{20}$ fatty acid mono-, di, or tri-glycerides from a vegetable oil or any mixture of two or more thereof;

c) a phospholipid and another surfactant; and d) a hydrophilic phase;

wherein component (a) has been wholly directly dissolved in component (b), component (b) is dispersed as tiny particles in component (d), and the composition is free from ethanol.

The invention also provides a preconcentrate for mixture with a hydrophilic phase to form a microemulsion of the invention, the preconcentrate composition comprising:

a) a water-insoluble pharmaceutically active material;

b) a $C_8$ to $C_{20}$ fatty acid mono-, di-, or tri-glyceride from a vegetable oil or any mixture of two or more thereof; and c) a phospholipid and another surfactant;

wherein component (a) is directly dissolved in component (b), and component (c) is such that, upon mixing the composition with a hydrophilic phase, a stable oil-in-water microemulsion is formed in which component (a) is in solution in the micro dispersed oil particles, the said preconcentrate being free from a hydrophilic phase.

The invention also provides a process for making a preconcentrate or microemulsion of the invention, wherein component (a) is dissolved directly in component (b) and not in component (d). It is to be understood that component (a) is dissolved directly in component (b) rather than first being dissolved in another liquid and the solution then mixed with component (b).

DESCRIPTION OF THE PREFERRED EMBODIMENTS

EP-A-327280 describes dissolving cyclosporin in a mono- or di-glyceride of a $C_6$–$C_{10}$ fatty acid. The solution can then be emulsified in an aqueous medium. However, these emulsions are not microemulsions and do not contain the mixture of lecithin and another surfactant which is especially used, together with the particular triglycerides component (b) all of which are necessary to obtain the significant advantages of the invention.

Microemulsions are transparent due to the very small particle size of the dispersed phase, typically less than 200 nm. Such small droplets produce only weak scattering of visible light when compared with that from the coarse droplets (1–10 m) of normal emulsions. An essential difference between microemulsions and emulsions is that microemulsions form spontaneously and, unlike emulsions, require little mechanical work in their formulation. General reviews on microemulsions are provided by Attwood, D. et al, J. Colloid Interface Sci. 46:249 and Kahlweit, M. et al, J. Colloid Interface Sci. 118:436.

In the present invention, component (a) is a water-insoluble pharmaceutically active material. The invention is particularly useful with the cyclosporins, e.g. cyclosporin A, dihydrocyclosporin C, cyclosporin D and dihydrocyclosporin D. It is also useful with other water-insoluble substances such as, for example, taxol.

In the compositions of the invention, component (a) is in solution in component (b). Component (b) can be a single glyceride or any mixture of glycerides (mono- and/or di- and/or tri-) derived from vegetable oils and containing $C_8$ to $C_{20}$ fatty acid residues. The preferred oils are coconut oil, peanut oil and castor oil. The whole oils can be used or the refined glycerides. The preferred glycerides are those containing $C_{12}$ to $C_{18}$ fatty acid residues, especially triglycerides, and these are the major components of the preferred oils.

The compositions of the three oils are as follows:
Castor Oil

| Tryglycerides of: | ricinoleic acid | 87% |
|---|---|---|
| | oleic acid | 7% |
| | linoleic acid | 3% |
| | palmitic acid | 2% |
| | stearic acid | 1% | and dihydroxystearic acid in trace amounts.
Coconut oil

Tryglycerides of mainly lauric and myristic acids with smaller proportions of capric, caproic acid, caprylic acid, oleic acid, palmitic acid and stearic acid.
Peanut oil

| Glycerides of: | oleic acid | 56% |
|---|---|---|
| | linoleic acid | 26% |
| | palmitic acid | 8.3% |
| | stearic acid | 3.1% |
| | arachidic acid | 2.4% |
| | behenic acid | 3.1% |
| | lignoceric acid | 1.1% | and capric and lauric acid in trace amounts.

Component (c) is a mixture of a phospholipid, preferably lecithin, and another surfactant to provide the stable microemulsion. Those skilled in the art will be aware of many surfactants which can be used, but we prefer to use polyoxyl 40 hydrogenated castor oil, polyoxyethylene-sorbitan monooleate, polyoxyethylene-sorbitan monopalmitate, polyoxyethylene-sorbitan monolaurate or polyoxyethylene-sorbitan monostearate. These surfactants are extremely effective with lecithin and are highly preferred. Any lecithin can be used but we prefer soya lecithin and egg lecithin. Hydroxylated lecithins are particularly suitable, especially when component (a) is a cyclosporin, since lecithin per se can be lipophilic to an extent sufficient to affect the desired spontaneous formation of a microemulsion.

In the microemulsions of the invention, component (d) is a hydrophilic phase. The preferred material is propylene glycol, but other substances can be used. Ethanol cannot be present. Water can of course also be present but it is not preferred. Despite the use of propylene glycol, component (a) remains wholly dissolved in the oil phase (component (b)).

In use, the microemulsion preconcentrates of the invention are diluted with aqueous liquid (e.g. water, fruit juice, milk etc) to form an oil-in-water microemulsion, e.g. for oral administration. This aids in ready absorption as the surface area of the globules is largely increased. The role played by bile salts in the initial step of fragmentation of fat globules, essential for fat digestion, is circumvented.

In the compositions of the invention, the polar phospholipid lecithin aids in emulsification of the fat and absorption of triglycerides into the GIT. The combination of HLB values of the polar lecithin and for example, the polyoxyl-40-hydrogenated castor oil, is very suitable for forming a balanced microemulsion.

The rate determining factor for the absorption of drug in the vehicle is not the enzymatic metabolism of triglycerides but rests primarily in the breakdown of the fat globules into micro particles since the enzymes (lipases) act mainly at the surface of the fat globules.

In the preconcentrates of the invention, the amounts of the components, in percent by weight, are as follows:

| | Component | General | Usual | Preferred |
|---|---|---|---|---|
| (a) | active pharmaceutical | 1–12% | 2.5–10% | 7–10% |
| (b) | oil phase | 20–80% | 30–60% | 40–50% |
| (c) | phospholipid | 1–10% | 3–8% | 5–6% |
| | other surfactant | 10–60% | 20–50% | 35–40% |

In the microemulsions, the weight percent of hydrophilic phase is generally up to about 75%, most usually from 15 to 50%, and preferably from 35 to 50%.

The weight ratio of component (a) to component (b) is preferably from 1:1 to 1:10, component (a) to the phospholipid preferably from 1:0.5 to 1:5.0, and component (a) to the surfactant preferably from 1:1 to 1:5.0.

The compositions can consist only of the components described, or they can contain other substances. For example, in order to prevent oxidation/rancidification of the natural oils, an antioxidant, e.g. α-tocopherol can be used. Propyl gallate may be used as an alternative.

In order that the invention may be more fully understood, the following Examples are given by way of illustration only.

EXAMPLES 1–4

Microemulsion preconcentrates were made of the substances indicated, by simple mixing. The cyclosporin A was completely dissolved in the oil phase in each case.

Preconcentrate 1

| Component | Parts |
|---|---|
| Castor oil | 3.0700 |
| Coconut oil | 1.6050 |
| Polyoxyl-40 Hydrogenated Castor oil | 3.7500 |
| Lecithin | 0.5650 |
| α-tocopherol | 0.0100 |
| Cyclosporin A | 1.0000 |

Preconcentrate 2

| Component | Parts |
|---|---|
| Castor oil | 3.1450 |
| Arachis oil | 1.5425 |
| Polysorbate-80 (Tween 80) | 3.7500 |
| Lecithin | 0.5525 |
| α-tocopherol | 0.0100 |
| Cyclosporine A | 1.0000 |

Preconcentrate 3

| Component | Parts |
|---|---|
| Castor oil | 4.1484 |
| Coconut oil | 2.0416 |
| Polyoxyl-40 Hydrogenated | 2.5000 |

-continued

| Component | Parts |
|---|---|
| Castor oil | |
| Lecithin | 0.3000 |
| α-tocopherol | 0.0100 |
| Cyclosporine A | 1.0000 |

Preconcentrate 4

| Component | Parts |
|---|---|
| Castor oil | 4.690 |
| Coconut oil | 1.500 |
| Polysorbate-80 (Tween 80) | 2.500 |
| Lecithin | 0.300 |
| α-tocopherol | 0.010 |
| Cyclosporin A | 1.000 |

When diluted with water or propylene glycol, or another hydrophilic substance, oil-in-water microemulsions formed spontaneously. There was no evidence of any insolubilization of the cyclosporin.

The microemulsion preconcentrates were filled into bottles to be administered as a drink solution using a syringe or more preferably with the aid of a metered dose pump with a droper actuator. The formulations were also encapsulated in soft gelatin capsules.

The compositions described in Examples 1 to 4 were subjected to stability examinations under accelerated conditions of temperature and humidity. The solutions were stored at RT (25° C.±2° C.), Ref, 40° C.—80% RH and 45° C. after filling into flint glass vials.

Simultaneously with the examination of solutions prepared according to the process of the invention, the stability of the commercially available Sandimmun Neoral capsules containing 100 mg cyclosporin A per capsule was also examined.

The quantative determination of cyclosporin A was performed by using HPLC method under the following conditions of chromatography:

| Pump | Waters -510 HPLC Pump |
|---|---|
| Detector | Waters -484 tunable absorbance detector |
| Injector | Waters -715 ultra wisp sample processor |
| Column | 4.6 mm × 25 cm column with L16 packing |
| Thermostat | 70° - For capsules |
| | 50° - For oral solution |
| Eluant | Filtered and degassed mixture of acetonitrile water, methanol and phosphoric acid (550:400:50:0.5) |
| Flow rate | 1 ml/min of the eluant |
| Integrator | Waters -746 |

It was observed from the above examinations that the stability of solutions prepared according to the process of the invention did not differ from the stability of the commercially available composition.

EXAMPLES 5–9

Microemulsions of the invention were made of the compositions indicated, by dissolving the cyclosporin A in the oils and then forming the oil-in-water emulsions. The procedure was:

(a) dissolve the cyclosporin A in the mixture of oils with slight warming and under stirring to obtain a clear yellow liquid. Confirm the complete dissolution of the drug by microscopy.

(b) add the surfactant and hydroxylated lecithin in that order, with stirring.

(c) add the propylene glycol with stirring. Stirring was continued for an hour to ensure the formation of a homogeneous translucent to opalescent microemulsion.

(d) add the alpha tocopherol and mix thoroughly.

EXAMPLE 5

Preparation of W/O microemulsion for administration in Soft Gelatin capsules:

| Component | Parts |
|---|---|
| Castor oil | 1.7200 |
| Coconut oil | 0.8000 |
| Polyoxyl-40 Hydrogenated Castor oil | 3.3512 |
| Lecithin | 0.4200 |
| α-tocopherol | 0.0088 |
| Propylene glycol | 1.5000 |
| Cyclosporin A | 1.0000 |

EXAMPLE 6

Preparation of O/W microemulsion for administration as oral solution:

| Component | Parts |
|---|---|
| Castor Oil | 1.2700 |
| Arachis oil | 0.6050 |
| Polysorbate-80 (Tween 80) | 3.7500 |
| Lecithin | 0.5525 |
| α-tocopherol | 2.0100 |
| Propylene glycol | 2.8125 |
| Cyclosporin A | 1.0000 |

EXAMPLE 7

Preparation of O/W microemulsion for administration as oral solution:

| Component | Parts |
|---|---|
| Castor oil | 1.3550 |
| Coconut oil | 0.6450 |
| Polyoxyl-40 Hydrogenated Castor oil | 3.7500 |
| Lecithin | 0.5525 |
| α-tocopherol | 0.0100 |
| Propylene glycol | 2.6875 |
| Cyclosporin A | 1.0000 |

EXAMPLE 8

Preparation of O/W microemulsion for administration as oral solution:

| Component | Parts |
|---|---|
| Castor oil | 0.800 |
| Coconut oil | 0.200 |
| Polysorbate-80 (Tween 80) | 2.490 |
| Lecithin | 0.300 |

-continued

| Component | Parts |
|---|---|
| α-tocopherol | 0.010 |
| Propylene glycol | 5.200 |
| Cyclosporin A | 1.000 |

EXAMPLE 9

Preparation of O/W microemulsion for administration as oral solution:

| Component | Parts |
|---|---|
| Castor oil | 1.200 |
| Coconut oil | 0.300 |
| Polyoxyl-40 Hydrogenated Castor oil | 2.490 |
| Lecithin | 0.300 |
| α-tocopherol | 0.010 |
| Propylene glycol | 4.700 |
| Cyclosporin A | 1.000 |

The oral solution which is filled into bottles can be administered using a syringe or more preferably with the aid of a metered dose pump with a dropper actuator.

The compositions described in Examples 5 to 9 were subjected to stability examinations under accelerated conditions of temperature and humidity. The solutions were stored at RT (25° C.±2° C.), Ref, 40° C.—80% RH and 45° C. after filling into flint glass vials.

Simultaneously with the examination of solutions prepared according to the process of the invention, the stability of the commercially available Sandimmun Neoral capsules containing 100 mg cyclosporin A per capsule was also examined.

The quantitative determination of cyclosporin A was performed by using HPLC method under the conditions previously noted (Examples 1 to 4).

It was observed from the above examination that the stability of solutions prepared according to the process of invention did not differ from the stability of the commercially available composition.

EXAMPLE 10

A drink formulation was made by taking an appropriate amount of the preconcentrate of Example 1 (to give the prescribed dose of cyclosporin A) and adding about 50 ml (or a glassful) of orange-flavoured cordial. The mixture was stirred and was then ready for oral consumption.

We claim:

1. A pharmaceutical composition in the form of a preconcentrate for mixture with a hydrophilic phase to form a microemulsion, which composition consists essentially of:

a) a water insoluble pharmaceutically active material;

b) $C_8$ to $C_{20}$ fatty acid mono-, di- or tri-glycerides from a vegetable oil or any mixture of two or more thereof; and c) a phospholipid and another surfactant;

wherein component (a) is directly dissolved in component (b) and wherein said preconcentrate further includes said component (c) such that, upon mixing the composition with a hydrophilic phase, a stable oil-in-water microemulsion is formed in which component (a) remains in solution in the micro dispersed oil particles and tendency to form solid microfine active material is reduced or totally absent with no precipitation of said active material taking place, said preconcentrate being free from a hydrophilic phase.

2. A pharmaceutical composition in the form of a stable oil-in-water microemulsion, which composition consists essentially of:

a) a water-insoluble pharmaceutically active material;

b) $C_8$ to $C_{20}$ fatty acid mono-, di- or tri-glycerides from a vegetable oil or any mixture of two or more thereof;

c) a phospholipid and another surfactant; and d) a hydrophilic phase;

wherein component (a) has been wholly directly dissolved in component (b), component (b) is dispersed as tiny particles in component (d), the composition is free from ethanol and component (a) remains in solution in component (b) with tendency to form solid microfine active material being reduced or totally absent with no precipitation of said active material taking place.

3. A composition according to claim 1, wherein component (a) is selected from the group consisting of a cyclosporin, or another water-insoluble peptide, or a water-insoluble antimicrobial or antineoplastic substance or mixtures thereof.

4. A composition according to claim 3, wherein component (a) is selected from the group consisting of cyclosporin A, dihydrocyclosporin C, cyclosporin D or dihydrocyclosporin D, or desmopresin, calcitonin, insulin, leuprolide, erythropoetin, a cephalosporin, vincristine, vinblastine, taxol or etoposide or mixtures thereof.

5. A composition according to claim 1, wherein in component (b) the glycerides are of $C_{12}$ to $C_{18}$ fatty acids.

6. A composition according to claim 1, wherein component (b) is whole castor oil, peanut oil or coconut oil, or is derived therefrom.

7. A composition according to claim 1, wherein the phospholipid in component (c) is lecithin.

8. A composition according to claim 7, wherein in component (c) the lecithin is hydroxylated lecithin.

9. A composition according to claim 1, wherein in component (c), said surfactant is selected from the group consisting of polyoxyl 40 hydrogenated castor oil, polyoxyethylene-sorbitan monooleate, polyoxyethylene-sorbitan monopalmitate, polyoxyethylene-sorbitan monolaurate or polyoxyethylene-sorbitan monosterate or mixtures thereof.

10. A composition according to claim 1 wherein the weight ratio of component (a) to component (b) is from 1:1 to 1:10.

11. A composition according to claim 1 wherein the weight ratio of component (a) to said phospholipid is from 1:0.5 to 1:5.0.

12. A composition according to claim 1 wherein the weight ratio of component (a) to said surfactant is from 1:1 to 1:5.0.

13. A process for making a composition according to claim 2, which comprises dissolving component (a) in component. (b) optionally with component (c), and then mixing the resulting solution with component (d) and component (c) if not included earlier.

14. A process according to claim 13, wherein a preconcentrate composition is mixed with component (d).

15. A soft gelatin capsule or oral administration fluid which comprises a composition as claimed in claim 2 and formulated in a form for oral administration.

16. An oral administration composition which comprises a composition as claimed in claim 2 and formulated in a form for oral administration.

17. A composition according to claim 7 wherein the lecithin is soya lecithin or egg lecithin.

18. A composition according to claim 2, wherein component (a) is selected from the group consisting of a cyclosporin, or another water-insoluble peptide, or a water-insoluble antimicrobial or antineoplastic substance or mixtures thereof.

19. A composition according to claim 18, wherein component (a) is selected from the group consisting of cyclosporin A, dihydrocyclosporin C, cyclosporin D or dihydrocyclosporin D, or desmopresin, calcitonin, insulin, leuprolide, erythropoietin, a cephalosporin, vincristine, vinblastine, taxol or etoposide or mixtures thereof.

20. The process of claim 14, wherein the preconcentrate comprises a) a water-insoluble pharmaceutically active material;

b) $C_8$ to $C_{20}$ fatty acid mono-, di- or tri-glycerides from a vegetable oil or any mixture of two or more thereof; and c) a phospholipid and another surfactant;

wherein component (a) is directly dissolved in component (b), and component (c) is such that, upon mixing the composition with a hydrophilic phase a stable oil-in-water microemulsion is formed in which component (a) is in solution in the micro dispersed oil particles, the said preconcentrate being free from a hydrophilic phase.

21. A composition according to claim 2, wherein said hydrophilic phase (d) includes propylene glycol.

22. Method of using the composition of claim 2, which comprises the step of orally administering the same.

23. A pharmaceutical composition for oral administration, which comprises a stable oil-in-water microemulsion of a) a water-insoluble pharmaceutically active cyclosporin:

b) $C_8$ to $C_{20}$ fatty acid mono,-di-, or tri-glycerides from a vegetable oil, or any mixture of two or more thereof;

c) a phospholipid and another surfactant; and d) a hydrophilic phase;

wherein the composition has been made by first forming a preconcentrate by directly dissolving component (a) in component (b), the preconcentrate also containing component (c) but being free from hydrophilic phase, and then mixing the preconcentrate with the hydrophilic phase, to form said stable oil-in-water microemulsion and wherein component (a) is wholly dissolved in component (b) and component (b) is dispersed as tiny particles in component (d), the composition being free from ethanol.

24. A composition according to claim 23, wherein component (a) is cyclosporin A, dihydrocyclosporin C, cyclosporin D or dihydrocyclosporin D;

in component (b), the glycerides are formed from $C_{12}$ to $C_{18}$ fatty acids; and in component (c), said phospholipid is lecithin and said surfactant is one of polyoxyl 40 hydrogenated castor oil, polyoxethylene-sorbitan monooleate, polyoxethylene-sorbitan monopalmitate, polyoxethylene-sorbitan monolaurate or polyoxethylene-sorbitan monostearate.

25. A composition according to claim 24, wherein in component (b) said vegetable oil is whole castor oil, peanut oil or coconut oil, or is derived therefrom; and the phospholipid in component (c) is soya lecithin, egg lecithin or hydroxylated lecithin.

26. A composition according to claim 25, wherein the weight ratio of component (a) to component (b) is from 1:1 to 1:10;

the weight ratio of component (a) to said phospholipid is from 1:0.5 to 1:5.0; and the weight ratio of component (a) to said surfactant is from 1:1 to 1:5.0.

27. A composition according to claim 25 in the form of a soft gelatin capsule or an oral administration fluid.

28. A method of making the pharmaceutical composition of claim 25 which comprises first forming a precencentrate by directly dissolving component (a) in component (b), the preconcentrate also containing component (c) but being free from hydrophilic phase, and then mixing the preconcentrate with the hydrophilic phase, to form said stable oil-in-water microemulsion and wherein component (a) is wholly dissolved in component (b) and component (b) is dispersed as tiny particles in component (d), the composition being free from ethanol.

* * * * *